(12) United States Patent
Ben-Muvhar

(10) Patent No.: US 9,744,059 B2
(45) Date of Patent: Aug. 29, 2017

(54) VASCULAR IMPLANT

(71) Applicant: Neovasc Medical Ltd., Or Yehuda (IL)

(72) Inventor: Shmuel Ben-Muvhar, D.N. Modin (IL)

(73) Assignee: NEOVASC MEDICAL LTD., Or Yehuda (IL)

( * ) Notice: Subject to any disclaimer, the term of this patent is extended or adjusted under 35 U.S.C. 154(b) by 0 days.

(21) Appl. No.: 14/542,311

(22) Filed: Nov. 14, 2014

(65) Prior Publication Data

US 2015/0073530 A1 Mar. 12, 2015

Related U.S. Application Data

(63) Continuation of application No. 13/250,968, filed on Sep. 30, 2011, now Pat. No. 8,911,489, which is a
(Continued)

(51) Int. Cl.
| | | |
|---|---|---|
| *A61F 2/82* | (2013.01) | |
| *A61F 2/07* | (2013.01) | |
| *A61F 2/89* | (2013.01) | |
| *A61B 17/122* | (2006.01) | |
| *A61B 17/128* | (2006.01) | |
| *A61F 2/95* | (2013.01) | |
| *A61F 2/962* | (2013.01) | |
| *A61F 2/966* | (2013.01) | |
| *A61F 2/06* | (2013.01) | |

(52) U.S. Cl.
CPC ............... *A61F 2/82* (2013.01); *A61F 2/07* (2013.01); *A61F 2/89* (2013.01); *A61B 17/1227* (2013.01); *A61B 17/1285* (2013.01); *A61F 2/95* (2013.01); *A61F 2/962* (2013.01); *A61F 2/966* (2013.01); *A61F 2002/068* (2013.01); *A61F 2002/075* (2013.01); *A61F 2002/826* (2013.01); *A61F 2220/0058* (2013.01); *A61F 2230/005* (2013.01); *A61F 2230/0054* (2013.01); *A61F 2230/0078* (2013.01); *A61F 2250/0039* (2013.01); *A61F 2250/0071* (2013.01)

(58) Field of Classification Search
CPC ........................... A61F 2/82; A61F 2250/0071
USPC ......... 623/1.11, 1.13, 1.15, 1.31, 1.12, 1.17; 606/108, 191, 194, 195, 198, 200
See application file for complete search history.

(56) References Cited

U.S. PATENT DOCUMENTS

| | | |
|---|---|---|
| 3,739,402 A | 6/1973 | Kahn et al. |
| 4,079,468 A | 3/1978 | Liotta et al. |

(Continued)

FOREIGN PATENT DOCUMENTS

| | | |
|---|---|---|
| DE | 102006052564 B3 | 12/2007 |
| GB | 1264471 A | 2/1972 |

(Continued)

OTHER PUBLICATIONS

International search report and written opinion dated Jan. 24, 2006 for PCT/IL2004/001063.

(Continued)

*Primary Examiner* — Vy Bui

(74) *Attorney, Agent, or Firm* — Wilson Sonsini Goodrich & Rosati

(57) ABSTRACT

A medical implant (20) includes first and second ring members (22, 24), each including a resilient framework (26) having a generally cylindrical form. A tubular sleeve (28) is fixed to the first and second ring members so as to hold the ring members in mutual longitudinal alignment, thereby defining a lumen (32) passing through the ring members. A constricting element (30) is fit around the sleeve at a location intermediate the first and second ring members so as to reduce a diameter of the lumen at the location.

5 Claims, 9 Drawing Sheets

Related U.S. Application Data continuation of application No. 10/595,926, filed as application No. PCT/IL2004/001063 on Nov. 18, 2004, now abandoned.

(56) References Cited

U.S. PATENT DOCUMENTS

| | | | |
|---|---|---|---|
| 4,204,283 A | 5/1980 | Bellhouse et al. | |
| 4,339,831 A | 7/1982 | Johnson | |
| 4,340,977 A | 7/1982 | Brownlee et al. | |
| 4,470,157 A | 9/1984 | Love | |
| 4,490,859 A | 1/1985 | Black et al. | |
| 4,580,468 A | 4/1986 | Gianturco | |
| 4,865,600 A | 9/1989 | Carpentier et al. | |
| 5,415,667 A | 5/1995 | Frater | |
| 5,593,424 A | 1/1997 | Northrup, II | |
| 5,618,301 A | 4/1997 | Hauenstein et al. | |
| 5,669,919 A | 9/1997 | Sanders et al. | |
| 5,755,769 A | 5/1998 | Richard et al. | |
| 5,824,041 A * | 10/1998 | Lenker | A61F 2/91 606/195 |
| 5,868,782 A | 2/1999 | Frantzen | |
| 5,876,448 A | 3/1999 | Thompson et al. | |
| 6,042,606 A | 3/2000 | Frantzen | |
| 6,086,612 A | 7/2000 | Jansen | |
| 6,113,631 A | 9/2000 | Jansen | |
| 6,120,534 A | 9/2000 | Ruiz | |
| 6,241,757 B1 * | 6/2001 | An | A61F 2/90 623/1.1 |
| 6,270,521 B1 * | 8/2001 | Fischell | A61F 2/95 623/1.11 |
| 6,312,465 B1 | 11/2001 | Griffin et al. | |
| 6,350,277 B1 * | 2/2002 | Kocur | 623/1.11 |
| 6,358,277 B1 | 3/2002 | Duran | |
| 6,458,153 B1 | 10/2002 | Bailey et al. | |
| 6,561,969 B2 | 5/2003 | Frazier et al. | |
| 6,610,088 B1 | 8/2003 | Gabbay | |
| 6,663,664 B1 * | 12/2003 | Pacetti | 623/1.2 |
| 6,726,703 B2 | 4/2004 | Broome et al. | |
| 6,764,505 B1 | 7/2004 | Hossainy et al. | |
| 6,875,231 B2 | 4/2005 | Anduiza et al. | |
| 6,929,660 B1 | 8/2005 | Ainsworth et al. | |
| 7,186,265 B2 | 3/2007 | Sharkawy et al. | |
| 7,232,459 B2 | 6/2007 | Greenberg | |
| 7,524,330 B2 | 4/2009 | Berreklouw | |
| 7,594,926 B2 * | 9/2009 | Linder | A61F 2/013 606/200 |
| 7,731,742 B2 | 6/2010 | Schlick et al. | |
| 8,303,617 B2 * | 11/2012 | Brady | A61F 2/013 606/200 |
| 8,911,489 B2 | 12/2014 | Ben-Muvhar | |
| 2001/0007956 A1 | 7/2001 | Letac et al. | |
| 2002/0032481 A1 | 3/2002 | Gabbay | |
| 2003/0105517 A1 | 6/2003 | White et al. | |
| 2003/0114913 A1 | 6/2003 | Spenser et al. | |
| 2003/0176914 A1 | 9/2003 | Rabkin et al. | |
| 2004/0093060 A1 | 5/2004 | Seguin et al. | |
| 2004/0102842 A1 | 5/2004 | Jansen | |
| 2004/0117009 A1 | 6/2004 | Cali et al. | |
| 2004/0193261 A1 | 9/2004 | Berreklouw | |
| 2004/0215325 A1 | 10/2004 | Penn et al. | |
| 2004/0225353 A1 | 11/2004 | McGuckin, Jr. et al. | |
| 2004/0236411 A1 | 11/2004 | Sarac et al. | |
| 2004/0236412 A1 | 11/2004 | Brar et al. | |
| 2004/0243230 A1 | 12/2004 | Navia et al. | |
| 2005/0075727 A1 | 4/2005 | Wheatley | |
| 2005/0107872 A1 | 5/2005 | Mensah et al. | |
| 2005/0137686 A1 | 6/2005 | Salahieh et al. | |
| 2005/0137690 A1 | 6/2005 | Salahieh et al. | |
| 2005/0159811 A1 | 7/2005 | Lane | |
| 2005/0182486 A1 | 8/2005 | Gabbay | |
| 2006/0020247 A1 | 1/2006 | Kagan et al. | |
| 2006/0020327 A1 | 1/2006 | Lashinski et al. | |
| 2006/0058872 A1 | 3/2006 | Salahieh et al. | |
| 2006/0095115 A1 | 5/2006 | Bladillah et al. | |
| 2006/0149360 A1 | 7/2006 | Schwammenthal et al. |
| 2006/0195183 A1 | 8/2006 | Navia et al. |
| 2006/0241745 A1 | 10/2006 | Solem |
| 2006/0259135 A1 | 11/2006 | Navia et al. |
| 2006/0259136 A1 | 11/2006 | Nguyen et al. |
| 2006/0293745 A1 | 12/2006 | Carpentier et al. |
| 2007/0027525 A1 | 2/2007 | Ben-Muvhar |
| 2007/0043435 A1 | 2/2007 | Seguin et al. |
| 2007/0050021 A1 | 3/2007 | Johnson |
| 2007/0142906 A1 | 6/2007 | Figulla et al. |
| 2007/0255394 A1 | 11/2007 | Ryan |
| 2007/0293940 A1 | 12/2007 | Schaeffer et al. |
| 2008/0071361 A1 | 3/2008 | Tuval et al. |
| 2008/0082164 A1 | 4/2008 | Friedman |
| 2008/0097571 A1 | 4/2008 | Denison et al. |
| 2008/0147179 A1 | 6/2008 | Cai et al. |
| 2008/0177381 A1 | 7/2008 | Navia et al. |
| 2008/0183273 A1 | 7/2008 | Mesana et al. |
| 2008/0228254 A1 | 9/2008 | Ryan |
| 2008/0243245 A1 | 10/2008 | Thambar et al. |
| 2009/0005863 A1 | 1/2009 | Goetz et al. |
| 2009/0082844 A1 | 3/2009 | Zacharias et al. |
| 2009/0138079 A1 | 5/2009 | Tuval et al. |
| 2009/0171456 A1 | 7/2009 | Kveen et al. |
| 2009/0188964 A1 | 7/2009 | Orlov |
| 2009/0216314 A1 | 8/2009 | Quadri |
| 2009/0276040 A1 | 11/2009 | Rowe et al. |
| 2009/0281618 A1 | 11/2009 | Hill et al. |
| 2009/0287296 A1 | 11/2009 | Manasse |
| 2009/0287299 A1 | 11/2009 | Tabor et al. |
| 2009/0292350 A1 | 11/2009 | Eberhardt et al. |
| 2009/0306768 A1 | 12/2009 | Quadri |
| 2010/0036479 A1 | 2/2010 | Hill et al. |
| 2010/0082094 A1 | 4/2010 | Quadri et al. |
| 2010/0191326 A1 | 7/2010 | Alkhatib |
| 2010/0217382 A1 | 8/2010 | Chau et al. |
| 2010/0249894 A1 | 9/2010 | Oba et al. |
| 2010/0305685 A1 | 12/2010 | Millwee et al. |
| 2011/0004296 A1 | 1/2011 | Lutter et al. |
| 2011/0208297 A1 | 8/2011 | Tuval et al. |
| 2011/0264196 A1 | 10/2011 | Savage et al. |
| 2012/0022637 A1 | 1/2012 | Ben-Muvhar |
| 2012/0041550 A1 | 2/2012 | Salahieh et al. |
| 2012/0101572 A1 | 4/2012 | Kovalsky et al. |
| 2012/0271398 A1 | 10/2012 | Essinger et al. |
| 2012/0303116 A1 | 11/2012 | Gorman, III et al. |
| 2013/0053950 A1 | 2/2013 | Rowe et al. |
| 2013/0304200 A1 | 11/2013 | McLean et al. |
| 2013/0310928 A1 | 11/2013 | Morriss et al. |
| 2014/0222136 A1 | 8/2014 | Geist et al. |

FOREIGN PATENT DOCUMENTS

| | | |
|---|---|---|
| GB | 1315844 A | 5/1973 |
| WO | WO 97/36556 A1 | 10/1997 |
| WO | WO 01/72239 A2 | 10/2001 |
| WO | WO 03/028522 A2 | 4/2003 |
| WO | WO 2004/058097 A2 | 7/2004 |
| WO | WO-2007058857 A2 | 5/2007 |
| WO | WO-2008005535 A2 | 1/2008 |
| WO | WO-2009033469 A1 | 3/2009 |
| WO | WO-2009053497 A1 | 4/2009 |
| WO | WO-2010057262 A1 | 5/2010 |
| WO | WO-2012035279 A1 | 3/2012 |

OTHER PUBLICATIONS

European search report and opinion dated Mar. 7, 2008 for EP Application No. 04799370.4.
Office action dated Mar. 31, 2011 for U.S. Appl. No. 10/595,926.
Office action dated May 16, 2013 for U.S. Appl. No. 13/250,968.
Office action dated Aug. 20, 2013 for U.S. Appl. No. 13/250,968.
Office action dated Mar. 6, 2014 for U.S. Appl. No. 13/250,968.
European search report and search opinion dated Jun. 16, 2014 for EP Application No. 14164803.0.
Al-Attar. Next generation surgical aortic biological prostheses: sutureless valves. European Society of Cardiology. Dec. 21, 2011, 10(14):1-3.

(56) References Cited

OTHER PUBLICATIONS

Banai, et al. Tiara: a novel catheter-based mitral valve bioprosthesis: initial experiments and short-term pre-clinical results. J Am Coll Cardiol. Oct. 9, 2012;60(15):1430-1. doi: 10.1016/j.jacc.2012.05.047. Epub Sep. 12, 2012.

Berreklouw, et al. Sutureless mitral valve replacement with bioprostheses and Nitinol attachment rings: feasibility in acute pig experiments. J Thorac Cardiovasc Surg. Aug. 2011;142(2):390-5.e1. doi: 10.1016/j.jtcvs.2010.12.018. Epub Feb. 4, 2011.

Boudjemline, et al. Steps toward the percutaneous replacement of atrioventricular valves an experimental study. J Am Coll Cardiol. Jul 19, 2005; 46(2):360-5.

Brinkman, et al. Transcatheter cardiac valve interventions. Surg Clin North Am. Aug. 2009;89(4):951-66, x. doi: 10.1016/j.suc.2009.06.004.

CardiAQ Valve Technologies to pursue first-in-man studies of its transcatheter mitral valve system. Cardiac Interventions Today. Jan. 12, 2010.

Chiam, et al. Percutaneous transcatheter aortic valve implantation: assessing results, judging outcomes, and planning trials: the interventionalist perspective. JACC Cardiovasc Interv. Aug. 2008;1(4):341-50. doi: 10.1016/j.cin.2008.03.018.

Condado, et al. Percutaneous treatment of heart valves. Rev Esp Cardiol. Dec. 2006;59(12):1225-31.

CoreValve USA. An advanced TAVR design. Medtronic.com Accessed Jan. 27, 2015.

De Backer, et al. Percutaneous transcatheter mitral valve replacement: an overview of devices in preclinical and early clinical evaluation. Circ Cardiovasc Interv. Jun. 2014;7(3):400-9. doi: 10.1161/CIRCINTERVENTIONS.114.001607.

Edwards Lifesciences 2005 annual report. Accessed Jan. 27, 2015.

Fanning, et al. Transcatheter aortic valve implantation (TAVI): valve design and evolution. Int J Cardiol. Oct. 3, 2013;168(3):1822-31. doi: 10.1016/j.ijcard.2013.07.117. Epub Aug. 20, 2013.

Gillespie, et al. Sutureless mitral valve replacement: inital steps toward a percutaneous procedure. Ann Thorac Surg. Aug. 2013;96(2):670-4. doi: 10.1016/j.athoracsur.2013.02.065.

Grube, et al. Percutaneous implantation of the CoreValve self-expanding valve prosthesis in high-risk patients with aortic valve disease: the Siegburg first-in-man study. Circulation. Oct. 10, 2006;114(15):1616-24. Epub Oct. 2, 2006.

Harmon, et al. Effect of acute myocardial infarction on the angle between the mitral and aortic valve plane. Am J Cardiol. Aug. 1, 1999;84(3):342-4, A8.

Herrman. Trancatheter mitral valve implantation. Cardiac Interventions Today. Aug./Sep. 2009; 81-85.

Ionasec, et al. Personalized modeling and assessemt of the aortic-mitral coupling from 4D TEE and CT. Med Image Comput Comput Assist Interv. 2009;12(Pt 2):767-75.

Karmi, et al. Percutaneous Valve Therapies. SIS 2007 Year book. Chapter 11. 11 pages.

Kumar, et al. Design considerations and quantitative assessment for the development of percutaneous mitral valve stent. Med Eng Phys. Jul. 2014;36(7):882-8. doi: 10.1016/j.medengphy.2014.03.010. Epub Apr. 16, 2014.

Lauten; et al., "Experimental evaluation of the JenaClip transcatheter aortic valve.", Sep. 1, 2009, 74(3), 514-9.

Leon, et al. Transcatheter aortic valve replacement in patients with critical aortic stenosis: rationale, device descriptions, early clinical experiences, and perspectives. Semin Thorac Cardiovasc Surg. 2006 Summer;18(2):165-74.

Lozonschi, et al. Transapical mitral valved stent implantation. Ann Thorac Surg. Sep. 2008;86(3)745-8. doi 10.1016/j.athoracsur.2008.05.039.

Lutter, et al. Off-pump transapical mitral valve replacement. Eur J Cardiothorac Surg. Jul. 2009;36(1):124-8; discussion 128. doi: 10.1016/j.ejcts.2009.02.037. Epub Apr. 25, 2009.

Lutter, et al. Transapical mitral valve implantation: the Lutter valve. Heart Lung Vessel. 2013;5(4):201-6.

Ma, et al. Double-crowned valved stents for off-pump mitral valve replacement. Eur J Cardiothorac Surg. Aug. 2005;28(2):194-8; discussion 198-9.

Maisano, et al. Mitral transcatheter technologies. Rambam Maimonides Med J. Jul. 25, 2013;4(3):e0015. doi: 10.5041/RMMJ.10115. Print Jul. 2013.

Navia, et al. Sutureless implantation a expandable mitral stent-valve prosthesis in acute animal model. TCT728. JACC. Nov. 8, 2011. vol. 58, No. 20 Suppl B. B194.

Orton. Mitralseal: hybrid trancatheter mitral valve replacement. Colorado State University. 2011; 311-312. https://www.acvs.org/files/proceedings/2011/data/papers/102.pdf.

Piazza, et al. Anatomy of the aortic valvar complex and its implication for transcatheter implantation of the aortic valve. Circ Cardiovasc Interv. Aug. 2008;1(1):74-81. doi: 10.1161/CIRCINTERVENTIONS.108.780858.

Pluth, et al. Aortic and mitral valve replacement with cloth-covered Braunwald-Cutter prosthesis. A three-year follow-up. Ann Thorac Surg. Sep. 1975;20(3):239-48.

Preston-Maher, et al. A Technical Review of Minimally Invasive Mitral Valve Replacements. Cardiovasc Eng Technol. 2015;6(2):174-184. Epub Nov. 25, 2014.

Quadri, et al. CVT is developing a non-surgical approach to replacing mitral valves that may be the alternative to open-chest surgery. CardiAQ Valve Technologies. May 8, 2009.

Ribiero, et al. Balloon-expandable prostheses for transcatheter aortic valve replacement. Prog Cardiovasc Dis. May-Jun. 2014;56(6):583-95. doi: 10.1016/j.pcad.2014.02.001. Epub Mar. 1, 2014.

Seidel, et al. A mitral valve prosthesis and a study of thrombosis on heart valves in dogs. J Surg Res. May 1962;2:168-75.

Shuto, et al. Percutaneous transvenous Melody valve-in-ring procedure for mitral valve replacement. J Am Coll Cardiol. Dec. 6, 2011; 58(24):2475-80. doi: 10.1016/j.jacc.2011.09.021.

Sondergaard, et al. First-in-human CardiAQ transcatheter mitral valve implantation via transapical approach. TCT-811. JACC. Sep. 13, 2014. vol. 64, No. 11 Suppl B. B237.

Spencer, et al. Surgical treatment of valvular heart disease. Part V. Prosthetic replacement of the mitral valve. American Heart Journal. Oct. 1968; 76(4):576-580.

Spillner, et al. New sutureless 'artial mitral-valve prosthesis' for minimally invasive mitral valve therapy. Textile Research Journal. 2010:1-7.

Tavr. Engager system. Precise Valve positioning. Accessed Jan. 28, 2015.

The JenaValve—the prosthesis. JenaValve Technology. Accessed Jan. 28, 2015.

Timek, et al. Aorto-mitral annular dynamics. Ann Thorac Surg. Dec. 2003;76(6):1944-50.

Tsang, et al. Changes in aortic-mitral coupling with severe aortic stenosis. JACC. Mar. 9, 2010; vol. 55. Issue 1A.

Veronesi, et al. A study of functional anatomy of aortic-mitral valve coupling using 3D matrix transesophageal echocardiography. Circ Cardiocasc Imaging. Jan. 2009;2(1):24-31. doi: 10.1161/CIRCIMAGING.108.785907. Epub Dec. 2, 2008.

Vu, et al. Novel sutureless mitral valve implantation method involving a bayonet insertion and release mechanism: a proof of concept study in pigs. J Thorac Cardiovasc Surg. Apr. 2012;143(4):985-8. doi: 10.1016/j.jtcvs.2012.01.037. Epub Feb. 11, 2012.

Walther, et al. Transapical approach for sutureless stent-fixed aortic valve implantation experimental results. Eur J Cardiothorac Surg. May 2006;29(5):703-8. Epub Apr. 5, 2006.

Webb, et al. Transcatheter aortic valve implantation: the evolution of prostheses, delivery systems and approsches. Arch Cardiocasc Dis. Mar. 2012;105(3):153-9. doi:10.1016/j.acvd.2012.02.001. Epub Mar. 16, 2012.

\* cited by examiner

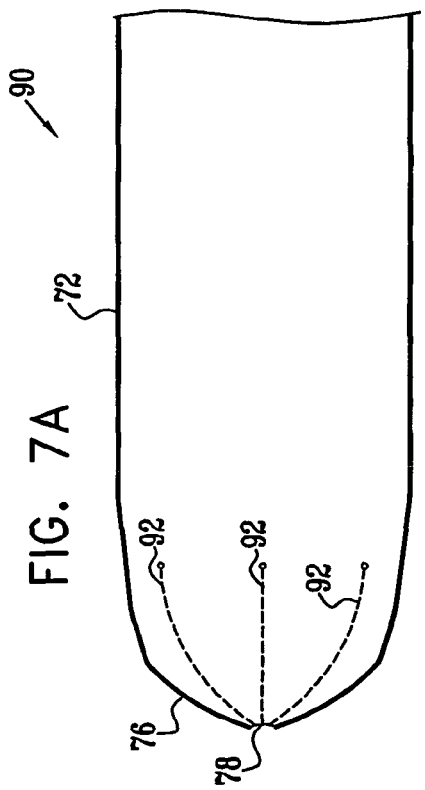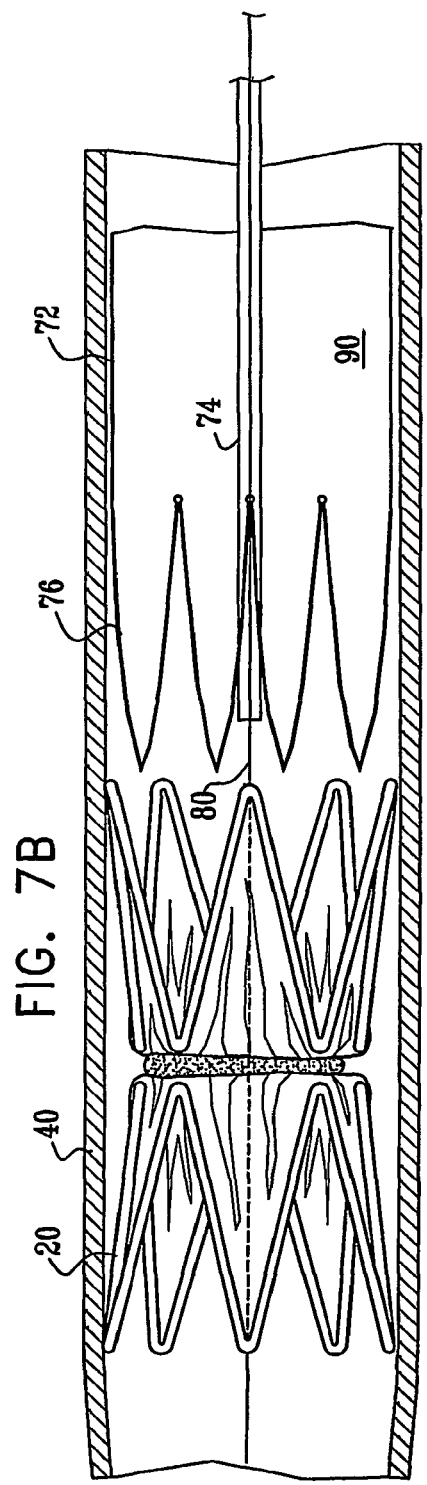

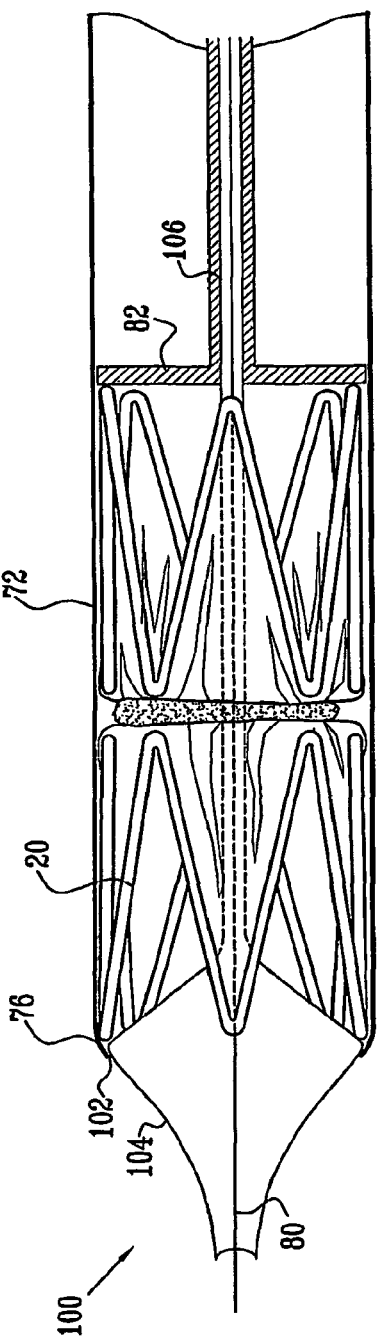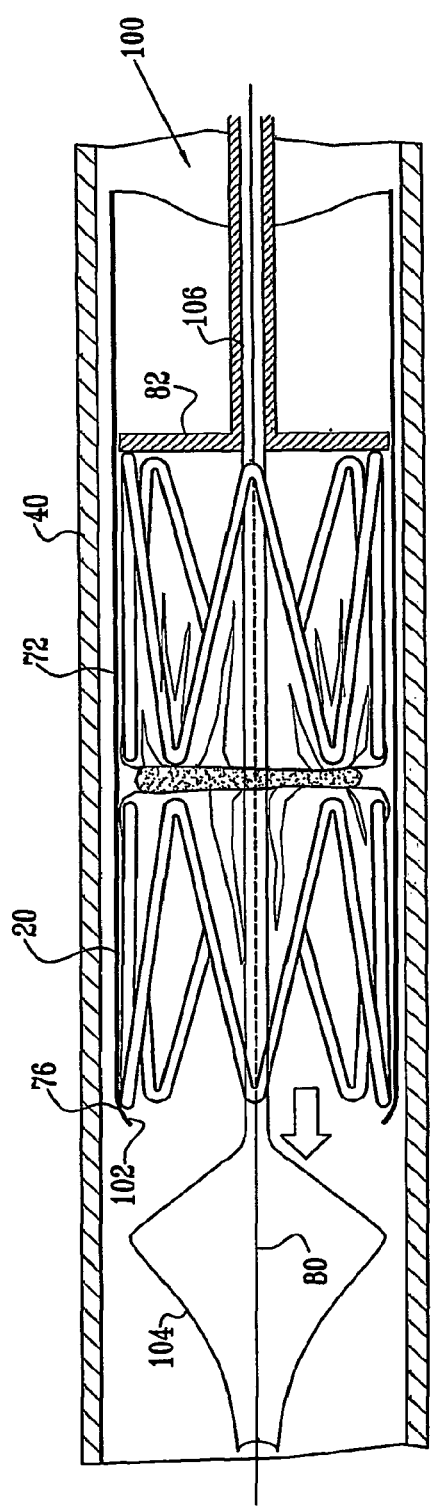

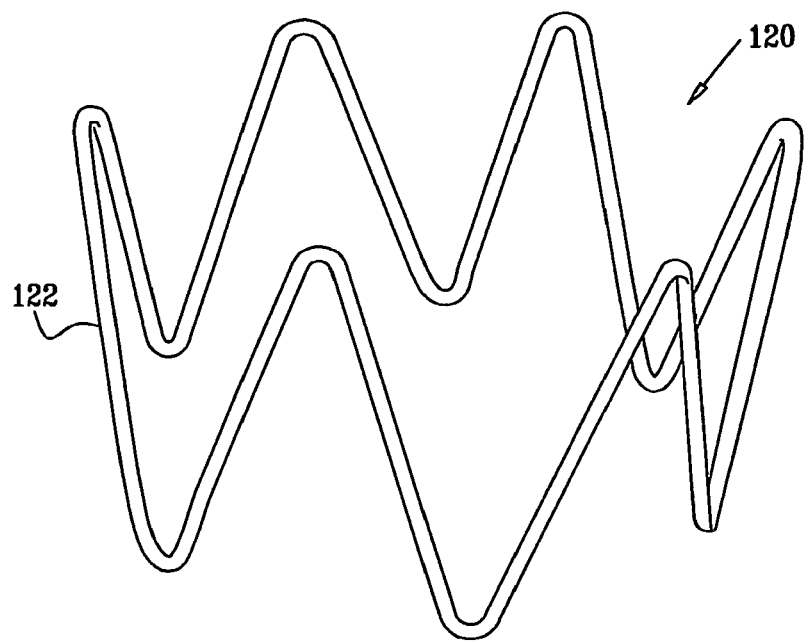
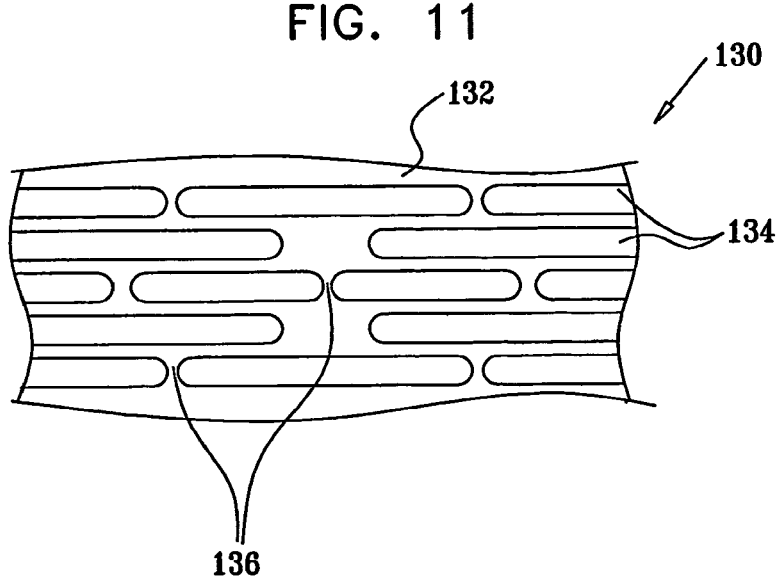

VASCULAR IMPLANT

CROSS-REFERENCE

This application is a continuation application of Ser. No. 13/250,968, filed Sep. 30, 2011, which is a continuation application of Ser. No. 10/595,926 filed Jul. 12, 2006, which is a US National State application of International Application No. PCT/IL2004/0010 filed Nov. 18, 2004 which claims priority to Israeli Application No. 158960 filed Nov. 19, 2003 incorporated herein by reference in its entirety and to which application we claim priority under 35 USC §120.

FIELD OF THE INVENTION

The present invention relates generally to implantable therapeutic devices, and specifically to intravascular implants.

BACKGROUND OF THE INVENTION

Stent implants are commonly used in treating arterial stenoses and other unwanted constrictions of body passages. Stents typically comprise a metal coil or mesh. An arterial stent, for example, is threaded through the vascular system to the point of stenosis in an artery. When the stent is in place, it is expanded to force the artery open to the desired diameter.

On the other hand, there are some procedures in which stent implants are required to constrict the diameter of a blood vessel. For example, Ruiz describes an endoluminal stent having adjustable constriction in U.S. Pat. No. 6,120,534, whose disclosure is incorporated herein by reference. The stent comprises a deformable mesh having a conical portion and a constricted region, which forms a flow-limiting constriction. The stent is delivered and deployed inside a blood vessel. The constricted region of the mesh is then selectively enlarged to adjust the flow impedance in the vessel. Ruiz describes particularly the use of his, stent to reduce blood flow in the pulmonary artery, as a palliative treatment for infants having complex congenital cardiac malformations.

Other types of constricting stents and applications of such stents are described by Shalev et al. in PCT Patent Publication WO 01/72239, whose disclosure is incorporated herein by reference. In particular, this publication describes the use of a flow-reducing implant in the coronary sinus, in order to promote angiogenesis in the heart tissues. The implant is inserted by catheter through a central vein, such as the jugular vein and brought into the coronary sinus. Alternatively, the implant may be installed in one or more of the coronary veins. Once the implant is in place, it is allowed to elastically expand or is plastically expanded using a balloon.

SUMMARY OF THE INVENTION

Embodiments of the present invention provide a constricting implant that is simple and inexpensive to manufacture, and can be deployed easily in the blood vessels, as well as in other body passages. The implant comprises a pair of generally-cylindrical ring members, which are fixed to a tubular sleeve so as to define a lumen passing through the ring members and the sleeve. The ring members each comprise a framework made of a resilient material, which can be compressed while the implant is inserted into the desired location in the blood vessel, and then expands either elastically or plastically to roughly the full diameter of the vessel. The sleeve comprises a flexible material, such as a fabric. The ring members are positioned longitudinally along the sleeve so that there is a longitudinal gap in between the two ring members. A constricting element is fitted around the sleeve in this gap so as to reduce the diameter of the lumen in between the two ring members to less than the diameter of the vessel.

Thus, when the implant is inserted into the vessel (or other body passage), the ring members expand, along with the portion of the sleeve to which they are fixed. The part of the sleeve in the gap between the ring members, however, remains constricted due to the constricting element. This constricted area of the lumen typically reduces the flow of blood through the vessel. The implant is particularly useful for restricting blood flow in the coronary, sinus, as described in the above-mentioned PCT publication, but it may similarly be used in other veins and arteries, as well as in other medical applications. In some embodiments, the constricting element may be opened in situ within the blood vessel, so as permit the diameter of the implant to increase if and when the constriction is no longer desired.

There is therefore provided, in accordance with an embodiment of the present invention, a medical implant, including:

first and second ring members, each including a resilient framework having a generally cylindrical form;

a tubular sleeve, fixed to the first and second ring members so as to hold the ring members in mutual longitudinal alignment, thereby defining a lumen passing through, the ring members; and a constricting element, which is fit around the sleeve at a location intermediate the first and second ring members so as to reduce a diameter of the lumen at the location.

The framework may include a wire, which is bent in a serpentine form. Typically, the ring members are adapted to be inserted in a radially-compressed form through a body passage to a target position within the passage, and then to expand radially at the target position so as to open the lumen therethrough. The framework may include an elastic material, which is compressible to provide the radially-compressed form of the ring members, and which expands radially when released at the target position.

In one embodiment, the implant includes one or more longitudinal support members, fixed to the framework of the first and second ring members, alongside the sleeve, so as to join the first and second ring members together.

In a further embodiment, the sleeve includes a fabric, which is stitched to the framework of the first and second ring members.

In another embodiment, the lumen passing through the first and second ring members has first and second ends, and the framework is configured to provide elongate protrusions at one or more of the ends of the lumen. The sleeve may be cut at one or more of the first and second ends in conformance with the protrusions. For example, the sleeve may be cut at the first end in conformance with the protrusions, while the sleeve at the second end covers both the protrusions and interstices between the protrusions at the second end of the lumen.

The implant may be adapted to be implanted in a coronary sinus of a patient, so that a flow of blood through the coronary sinus is inhibited by the reduced diameter of the lumen.

In another aspect of the invention, the constricting element is adapted to expand under an outward radial force so as to permit the reduced diameter of the lumen to increase.

In one embodiment, the constricting element includes an elastic wire, having bends that are fastened shut so as to provide the reduced diameter, and which are adapted to open under the outward radial force.

There is also provided, in accordance with an embodiment of the present invention, method for producing a medical implant, including:

providing first and second ring members, each including a resilient framework having a generally cylindrical form;

fixing a tubular sleeve to the first and second ring members so as to hold the ring members in mutual longitudinal alignment, thereby defining a lumen passing through the ring members; and fitting a constricting element around the sleeve at a location intermediate the first and second ring members so as to reduce a diameter of the lumen at the location.

There is additionally provided, in accordance with an embodiment of the present invention, a method for restricting flow of a fluid through a body passage, including:

providing an implant including first and second ring members, each including a resilient framework having a generally cylindrical form, with a tubular sleeve, fixed to the first and second ring members so as to hold the ring members in mutual longitudinal alignment, passing the implant, in a radially-compressed form, through the body passage to a target position within the body passage; and causing the implant to expand radially at the target position so as to open the lumen therethrough.

Typically, passing the implant includes enclosing the implant within a catheter, which passes through the body passage, and causing the implant to expand includes ejecting the implant through an aperture in a distal end of the catheter. In some embodiments, the distal end of the catheter has generally conical shape, and ejecting the implant includes expanding the distal end so as to open the aperture so that the implant may pass therethrough. Alternatively, ejecting the implant includes tearing the distal end so as to open the aperture so that the implant may pass therethrough. Further alternatively, the distal end of the catheter includes an elastic plug, which closes the aperture while the catheter passes through the body passage, and ejecting the implant includes radially compressing the plug so as to open the aperture and to allow the lumen of the implant to pass over the plug.

In another aspect of the invention, the method includes exerting an outward radial pressure from within the implant after the implant has expanded in the target position so as to open the constricting element, thereby permitting the reduced diameter of the lumen to increase. Typically, exerting the outward radial pressure includes inserting a balloon into the lumen, and inflating the balloon.

There is further provided, in accordance with an embodiment of the present invention, apparatus for delivery of an implant to a target position in a body passage, the apparatus including:

an elongate, tubular sheath, which is adapted to be passed through the body passage while containing the implant in a compressed state inside the sheath, wherein the sheath has a distal end made of an elastic material in a generally conical shape with an aperture formed therein; and an ejector, which is adapted to force the implant in a distal direction, thus stretching the elastic material so as to expand the aperture, whereby the implant passes through the aperture.

There is moreover provided, in accordance with an embodiment of the present invention, apparatus for delivery of an implant to a target position in a body passage, the apparatus including:

an elongate, tubular sheath, which is adapted to be passed through the body passage while containing the implant in a compressed state inside the sheath, wherein the sheath has a distal end having a generally conical shape with an aperture formed therein; and an ejector, which is adapted to force the implant in a distal direction, thus causing the distal end of the sheath to tear so as to expand the aperture, whereby the implant passes through the aperture.

The distal end of the sheath may be scored with lines, along which the sheath tears.

There is furthermore provided, in accordance with an embodiment of the present invention, apparatus for delivery of an implant to a target position in a body passage, the apparatus including:

an elongate, tubular sheath, which is adapted to be passed through the body passage while containing the implant in a compressed state inside the sheath, wherein the sheath has a distal end with an aperture formed therein;

a lumen passing longitudinally through the sheath and through the implant contained within the sheath, such that a portion of the lumen at the distal end of the sheath, is distended so as to plug the aperture while the sheath passes through the body passage, the distended portion of the lumen including a flexible material; and an ejector, which is adapted to force the implant in a distal direction, thus ejecting the implant through the aperture and compressing the distended portion of the lumen, so that the implant passes over the lumen to the target position in the body passage.

There is also provided, in accordance with an embodiment of the present invention, apparatus for narrowing a body passage, the apparatus including:

a narrowing implant, which includes:

first and second ring members, each including a resilient framework having a generally cylindrical form;

a tubular sleeve, fixed to the first and second ring members so as to hold the ring members in mutual longitudinal alignment, thereby defining a lumen passing through the ring members; and a constricting element, which is fit around the sleeve at a location intermediate the first and second ring members so as to reduce a diameter of the lumen at the location; and a catheter for delivering the implant to a target position in the body passage.

There is additionally provided, in accordance with an embodiment of the present invention, a stent for implantation in a lumen, including:

a plurality of struts, with intervening openings therebetween; and narrow connecting pieces, bridging at least some of the openings so as to interconnect the struts, wherein exertion of a first outward radial force on the struts causes the stent to open to a first diameter by opening the intervening openings between the struts, and wherein the narrow connecting pieces are adapted to break under, exertion on the struts of a second, outward radial, force, greater than the first outward radial force, so that the stent opens to a second diameter, greater than the first diameter.

There is further provided, in accordance with an embodiment of the present invention, a method for narrowing a blood vessel, including:

inserting a catheter into the blood vessel;

deploying a clip outward from the catheter so that first and second ends of the clip engage respective first and second points on a wall of the blood vessel; and ejecting the clip from the catheter after the first and second, ends of the clip have engaged the first and second points, thus causing the ends of the clip to draw toward one another and thereby pinching together the first and second points.

The present invention will be more fully understood from the following detailed description of the embodiments thereof, taken together with the drawings in which:

BRIEF DESCRIPTION OF THE DRAWINGS

FIGS. 7A and 7B are schematic side views of a catheter used to deliver an implantable device to a target location in a blood vessel, in accordance with another embodiment of the present invention;

FIGS. 8A, 8B and 8C are schematic side views of a catheter used to deliver an implantable device to a target location in a blood vessel, in accordance with yet another embodiment of the present invention;

FIG. 10 is a schematic, pictorial illustration of a constricting ring that has been opened, in accordance with an embodiment of the present invention;

FIG. 11 is a schematic, detail view of a stent, in accordance with an alternative embodiment of the present invention;

DETAILED DESCRIPTION OF THE INVENTION

Figure 1:
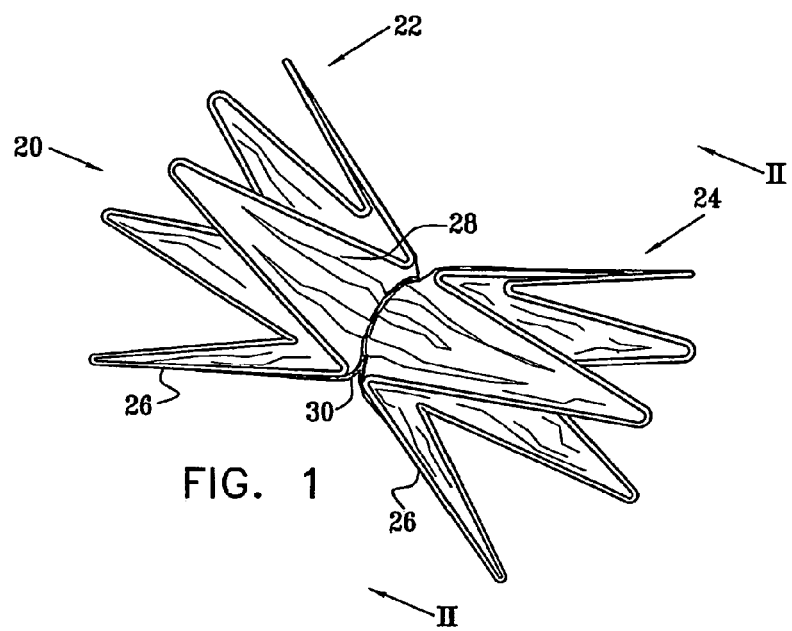
FIG. 1 is a schematic, pictorial view of an implantable device for restricting flow in a blood vessel, in accordance with an embodiment of the present invention.
Figure 2:
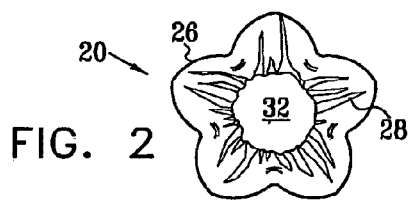
FIG. 2 is a schematic, cross-sectional view of the device of FIG. 1, taken along a line II-II.

Reference is now made to FIGS. 1 and 2, which schematically illustrate a device 20 for implantation in a body passage, in accordance with an embodiment of the present invention. FIG. 1 is a pictorial illustration of the device, while FIG. 2 is a cross-sectional view taken along a line 11-11 in FIG. 1. Device 20 is adapted for use particularly in restricting blood flow through the coronary sinus, as described in the above-mentioned PCT Publication WO 01/72239. Alternatively, devices in accordance with the principles of the present invention may be implanted elsewhere in the vascular system, as well as in other body passages. For the sake of simplicity and clarity, however, and not limitation, embodiments of the present invention are described hereinbelow with reference to implantation of flow-constricting devices in blood vessels, such as the coronary sinus.

Device 20 comprises ring elements 22 and 24, each of which comprises a resilient framework 26. Each framework defines a generally-cylindrical shape, although this shape is distorted by the mechanical constraints of the device, as described below. Therefore, the cylinders tend to widen at the ends of device 20 and narrow toward the middle, as shown in FIG. 1. In the pictured embodiments, framework 26 comprises a wire or thin rod, which is bent into a serpentine shape. Typically, the framework comprises an elastic material, which may be compressed or otherwise bent, but then returns to its original shape, as shown in the figure. Super-elastic materials, such as Nitinol, are useful for this purpose. Alternatively, the framework may comprise a resilient, deformable material, such as a suitable metal or plastic. Further alternatively or additionally, each framework 26 may comprise a mesh or coil, as is known in the art. In any case, the term "resilient" as used herein means that once device 20 is deployed within a body passage, framework 26 has sufficient mechanical strength to withstand normal forces exerted by the wall of the passage and by fluid flow within the passage, in the manner of stents known in the art.

Ring elements 22 and 24 are fixed to a flexible sleeve 28, which has a generally tubular form. Typically, sleeve 28 comprises a biocompatible fabric, such as Gore-Tex or Dacron, which is stitched or otherwise fastened to framework 26. Alternatively, other sleeve materials may be used, such as thin plastic or rubber materials. The sleeve is fixed to the ring elements in such a way as to form a lumen 32 (FIG. 2) through device 20. The sleeve is supported at each end of the lumen by one of the ring elements, while leaving a longitudinal gap in, the sleeve, typically several millimeters long, between the inner ends of the two ring elements. While the ring elements themselves are relatively stiff (due to the resilience of framework 26), device 20 can be bent and deformed freely within the gap region of the sleeve.

Figure 9A:
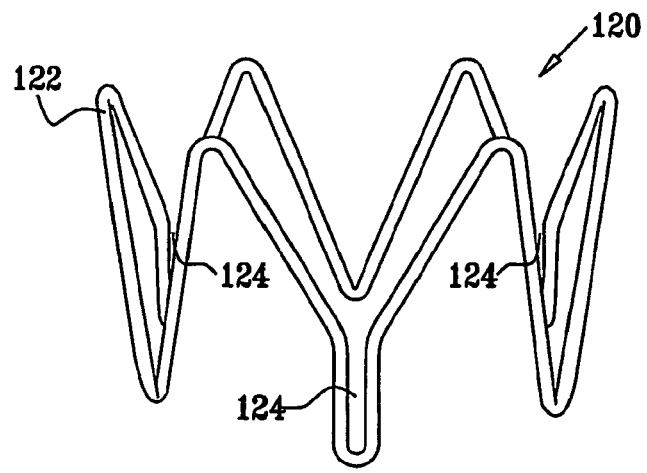
FIG. 9A is a schematic, pictorial illustration of a constricting ring, in accordance with an embodiment of the present invention.

A constricting element 30 is fitted around sleeve 28 within the gap region. As can be seen in FIG. 2, the effect of this constricting element is to reduce the diameter of lumen 32 to a predetermined size, less than the expanded diameter of ring elements 22 and 24. Constricting element 30 may simply comprise a thread, which is tied around the sleeve, or it may alternatively comprise a closed ring, made of plastic or metal. A constricting ring of this latter type is shown in FIG. 9A and described hereinbelow with reference thereto.

Figure 3:
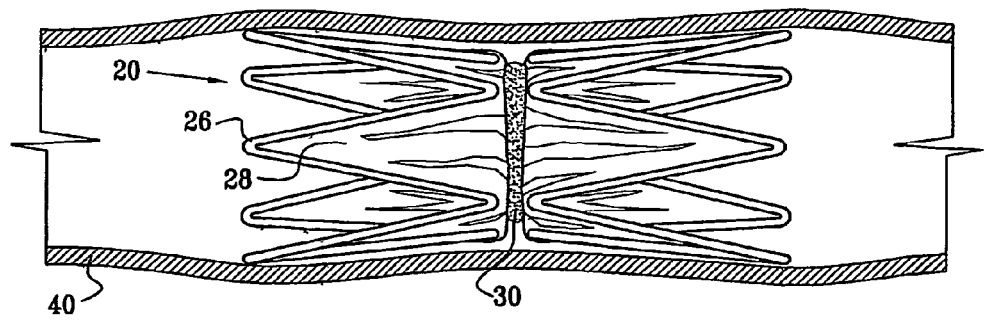
FIG. 3 is a schematic side view of the device of FIG. 1 implanted in a blood vessel

FIG. 3 is a schematic side view of device 20 after implantation inside a blood vessel 40. Typically, device 20 is passed through the vascular system to the appropriate location (such as the coronary sinus), using a suitable percutaneous catheter (not shown in the figures). Suitable methods of catheterization for this purpose are known in the art. During the insertion procedure, device 20 is compressed radially, so that its outer diameter is substantially smaller than the blood vessels through which it must pass. As noted above, device 20 is able to bend freely in the area of the gap between ring elements 22 and 24, where constricting element 30 is located. This bending capability generally makes it easier for the physician operating the catheter to pass the device through bends in the blood vessels.

Upon reaching the desired location in blood vessel 40, device 20 is released from the catheter. If framework 26 is made of an elastic material, such as Nitinol, the device will expand by itself, due to its own elasticity, as soon as it is released. Alternatively, if framework 26 comprises a malleable material, a balloon may be inflated within each of ring elements 22 and 24, or other means known in the art may be used, in order to expand the framework. The above-mentioned PCT publication describes special types of balloons that may be used for this purpose. As can be seen in FIGS. 1 and 3, the serpentine shape of framework 26 creates elongated "fingers" that protrude at the ends of device 20. Once the ring elements have expanded, these fingers press outward against the wall of the blood vessel, thus anchoring device 20 in place. Blood in vessel 40 flows through lumen 32, but flow is restricted by the constriction at constricting element 30. If device 2Q is deployed in the coronary sinus, for example, the flow restriction causes increased pressure in the coronary veins, thus promoting myocardial angiogenesis.

Device 20 may be left in place indefinitely, in substantially the form shown in FIG. 3. Alternatively, it may be desirable in some cases to eliminate the flow restriction caused, by the device. In such cases, it is not necessary to remove device 20 from the body. Rather, a catheter with a suitable cutting tool may be inserted percutaneously to the location of the device, and the cutting tool may then be used to cut constricting element 30. The constriction in the diameter of lumen 32 will then open up by itself.

Figure 4:
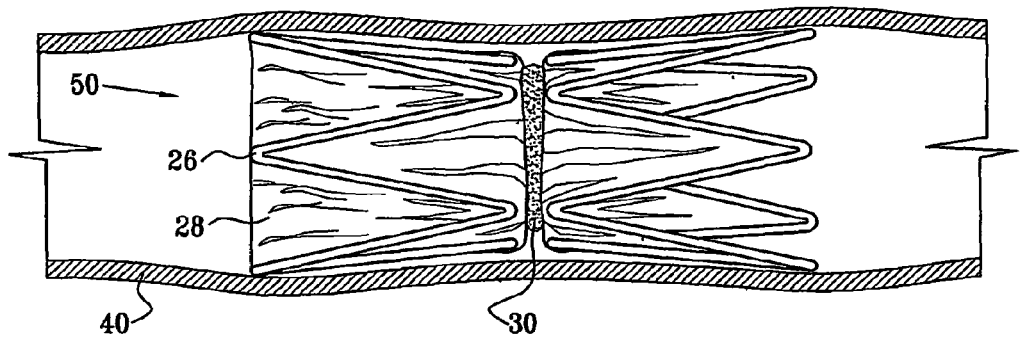
FIG. 4 is a schematic side view of a device for restricting flow, implanted in a blood vessel, in accordance with another embodiment of the present invention.

FIG. 4 is a schematic side view of an implantable device 50 after implantation inside blood vessel 40, in accordance with another embodiment of the present invention. Blood in vessel 40 is assumed to flow from left to right in the view of the figure. Device 50 is substantially identical to device 20, as described above, except for the shape of sleeve 28. In device 20, sleeve 28 is trimmed so that the ends of the sleeve have the same general shape as the "fingers" of framework 26. In device 50, however, sleeve 28 is trimmed to a generally straight edge at the upstream (left) end of the device, covering the interstices between the fingers, as well as the fingers themselves. The straight upstream edge can be useful in reducing blood leakage around the sides of the device, thus providing more complete and reliable flow restriction. The uneven shape of the sleeve is maintained on the downstream edge, in order to anchor device 50 securely to the walls of vessel 40 against the pressure exerted by the blood flow in the vessel. Alternatively, sleeve 28 may be cut in other configurations, as mandated by medical and mechanical considerations.

Figure 5:
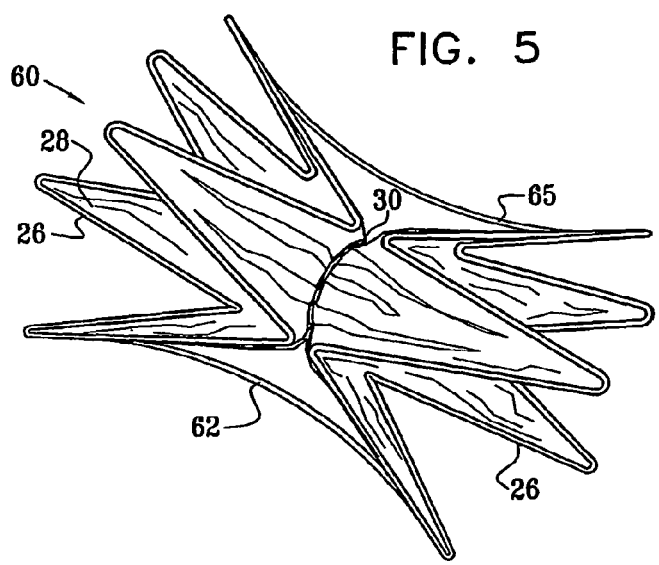
FIG. 5 is a schematic, pictorial view of an implantable device for restricting flow in a blood vessel, in accordance with still another embodiment of the present invention.

FIG. 5 is a schematic, pictorial view of an implantable device 60, in accordance with still another embodiment of the present invention. Device 60 is also substantially similar to device 20, as described above, except for the addition of longitudinal support members 62 and 65. The support members join ring elements 22 and 24 together and thus enhance the mechanical strength and stability of device 60. Although two longitudinal support members are shown in FIG. 5, greater or smaller numbers of supports members may be used in like fashion. Note, however, that in the gap between the ring elements, sleeve 28 is detached from the support members, so that the diameter of lumen 32 can still be reduced by constricting element 30.

Figure 6A:
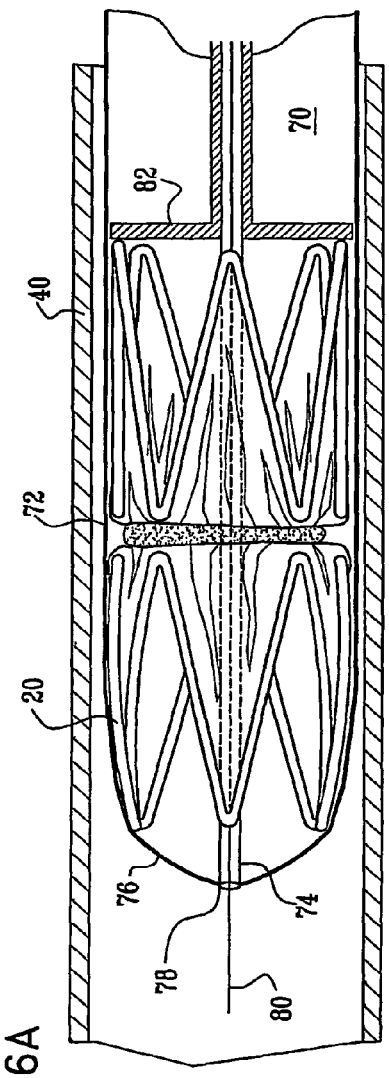
FIGS. 6A and 6B are schematic side views of a catheter used to deliver an implantable device to a target location in a blood vessel, in accordance with an embodiment of the present invention.
Figure 6B:
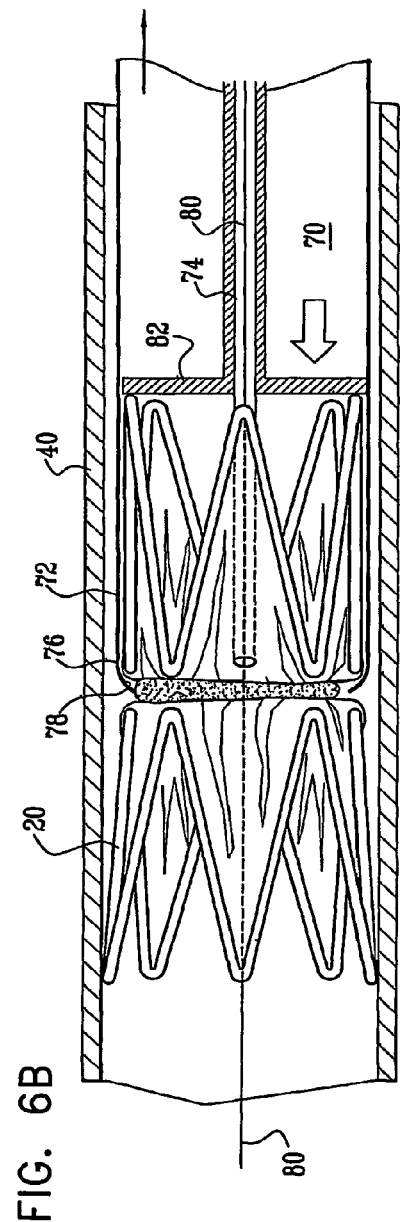

FIGS. 6A and 6B are schematic side views of a catheter 70, in a cutaway view, which is used to deliver device 20 to a target position in blood vessel 40, in accordance with an embodiment of the present invention. As shown in FIG. 6A, catheter 70 has a tubular outer shell 72 and a central lumen 74. Prior to delivery, device 20 is held inside shell 70, with lumen 74 passing through lumen 32 of device 20. A distal end 76 of shell 72 has a roughly conical shape, and has a small exit aperture 78 surrounding lumen 32.

Typically, to implant device 20 in vessel 40, an operator threads a guide wire 80 through a part of the patient's vascular system to the target position, as is known in the art. For example, the guide wire may be passed through the jugular vein into the coronary sinus. Once the guide wire is in place, the operator slides lumen 74 over the guide wire, and thus guides distal end 76 of catheter 70 to the target position. A contrast medium may be injected through lumen 74 or through another, parallel lumen (not shown) to aid the operator in visualizing vessel 40 during the procedure using a fluoroscope, as is known in the art.

When distal end 76 has reached the target position, the operator uses an ejector 82 to push device 20 out through aperture 78 in the distal end of the catheter. Distal end 76 in this embodiment is made of a material that is sufficiently elastic so that the aperture opens freely to the diameter of device 20. Once the device is ejected, it expands to the diameter of vessel 40, as shown in FIG. 3, and anchors itself in place. The operator then withdraws catheter 70, and distal end 76 contracts back roughly to its original form.

FIGS. 7A and 7B are schematic side views of another catheter 90, which is used to deliver device 20, in accordance with an alternative embodiment of the present invention. FIG. 7A shows the catheter before delivery of device 20, while FIG. 7B shows the catheter, after, the delivery. In this embodiment, distal end 76 comprises a thin sheath, which tears open as ejector 82 pushes the device out of the catheter. Optionally, as shown in FIG. 7A, the distal end is scored along lines 92, so that as device 20 is ejected, the distal end tears cleanly, in a predictable fashion. Once device 20 has been ejected, the distal end may remain open where it has torn, but the open distal does not interfere with withdrawal of catheter 90 along wire 80.

Figure 8C:
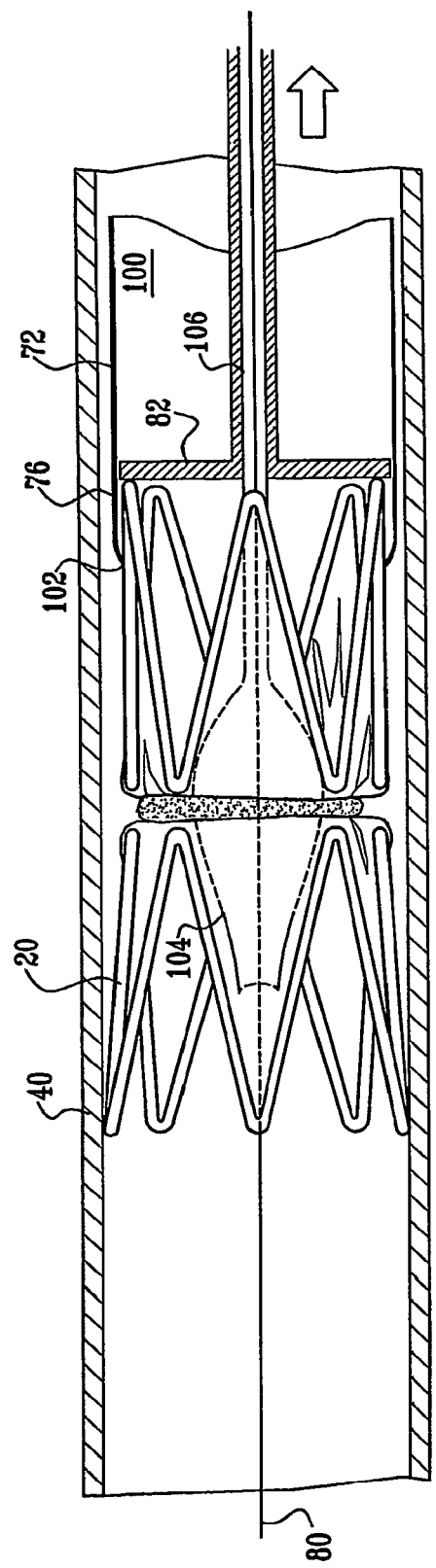

FIGS. 8A, 8B and 8C are schematic side views of a catheter 100 for delivering device 20, in accordance with yet another embodiment of the present invention. In this embodiment, distal end 76 has an aperture 102 that is large enough to accommodate the (compressed) diameter of device 20 when the device is ejected from the catheter. Until the catheter reaches the target position, however, the aperture is closed by a distended portion 104 of a lumen 106 that passes through the catheter, as shown in FIG. 8A. The lumen is typically used to accommodate a guide wire and/or to inject contrast medium, as described above. Distended portion 104 is made of a flexible material, which may be either elastic or malleable, and is shaped so as to plug aperture 102.

When distal end 76 reaches the target position, lumen 106 is advanced (and/or catheter 100 is withdrawn) so as to open aperture 102, as shown in FIG. 8B. Ejector 82 then pushes device 20 out through the aperture. As shown in FIG. 8C, portion 104 is sufficiently flexible so that as the narrow, gap region of lumen 32 through device 20 passes over it, portion 104 closes down so that lumen 32 can slide over it. Once device 20 has been implanted at the target position, portion 104 resumes its previous shape, and lumen 106 may be pulled back in the proximal direction in order to close aperture 102. Catheter 100 is then withdrawn from the body.

FIG. 9A is a schematic, pictorial illustration of a constricting ring 120, in accordance with an embodiment of the present invention. This ring may be used as a constricting element in device 20, taking the place of element 30 shown in the preceding figures. Ring 120 comprises a flexible, elastic wire 122. For example, wire 122 may comprise a super-elastic material, such as Nitinol. Wire 122 is formed with multiple bends, typically in a serpentine pattern, as shown in FIG. 9A. Some of the bends are closed bends 124, at which the wire segments on opposing sides of the bend are fixed together, thus narrowing the overall circumference of ring 120. When ring 120 is installed in place of element 30 on device 20, the narrowed circumference of the ring constricts the diameter of lumen 32, as shown in FIGS. 1 and 2.

Figure 9B:
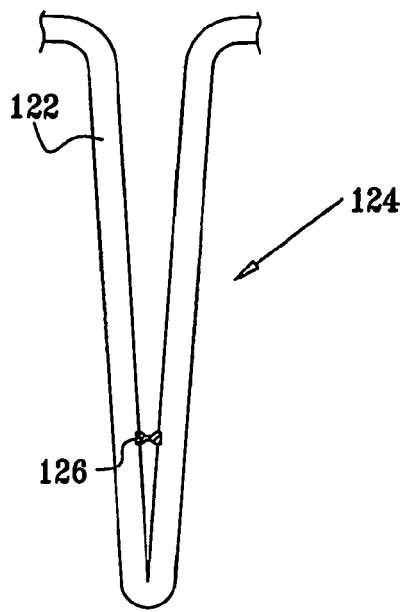
FIGS. 9B and 9C are schematic side views showing details of a constricting ring, in accordance with embodiments of the present invention.
Figure 9C:
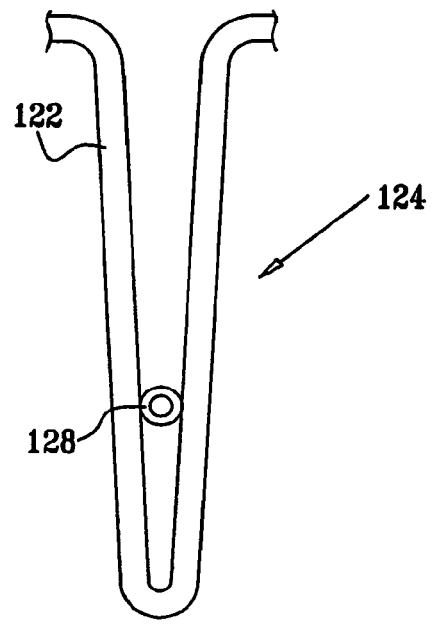

FIGS. 9B and 9C are schematic, detail views of one of closed bends 124 in ring 120, in accordance with two exemplary embodiments of the present invention. In the embodiment of FIG. 9B, the opposing segments of wire 122 are pulled together and then fastened by welding, glue or other means, at a fastening point 126. Laser micro-welding, as is known in the art, may be used for this purpose. In FIG. 9C, a connecting element 128, such as a miniature ring, is welded or otherwise fastened in place between the segments of wire on either side of the bend. In either case, bends 124 are typically closed weakly enough so that the fastening points or connecting elements will break open under outward radial pressure.

FIG. 10 is a schematic, pictorial illustration of ring 120 following opening of closed bends 124, in accordance with an embodiment of the present invention. The closed bends may be opened in situ, after device 20 has been implanted in a blood vessel. For this purpose, for example, a balloon catheter may be inserted into lumen 32 of device 20, and the balloon may be inflated with sufficient pressure to break open the fastening points of at least some of bends 124. Due to the elasticity of wire 122, ring 120 will then expand to the larger diameter shown in FIG. 10, and lumen 32 will open up accordingly. This sort of procedure may be used, for example, to permit free flow of blood through vessel 40 when the constriction due to device 20 is no longer needed or desired.

FIG. 11 is a schematic, detail view of a part of a stent 130, in accordance with another embodiment of the present invention. This embodiment also uses the principle of radial expansion of an intravascular implant that was described above. Stent 130 comprises a structure of struts 132 with intervening openings 134. Some of the openings are bridged by narrow connecting pieces 136. Stent 130 is initially collapsed and crimped over a balloon for insertion into the target blood vessel. Inflation of the balloon to a first, intermediate pressure causes the stent to expand radially outward, so that openings 134 between struts 132 open to the configuration shown in FIG. 11. The balloon is then withdrawn. The stent may be used in this configuration, for example, to open a blocked artery or other body lumen.

It often occurs after implantation of a stent that the body lumen in question once again becomes constricted, due to accretion of material inside the stent, for example. In this case, a balloon may once more be inserted inside stent 130 and inflated to a second, higher pressure. The balloon thus exerts an outward radial force on stent 130, causing one or more of connecting pieces 136 to break open. Thus, the diameter of stent 130 (and of the lumen it is supporting) is increased simply and safely.

Although in the embodiments described above, framework 26 and sleeve 28 are shown to have certain particular shapes, alternative shapes and forms of these elements, which will, be apparent to those skilled in the art, are considered to be within the scope of the present invention. Similarly, catheters of the general types described above may be used to deliver not only device 20, but also other implantable devices as described hereinabove and as are otherwise known in the art. On the other hand, although the catheters shown here provide convenient means for delivering implants in accordance with the present invention, such implants may also be delivered by other means, both minimally invasive (typically percutaneous) and invasive (i.e., surgical).

Methods for reducing the diameter or circumference of a vascular structure by surgical means are also known in the art. Methods of this sort are described, for example, in, U.S. Pat. No. 5,593,424 and U.S. Pat. No. 6,561,969, whose disclosure are incorporated herein by reference. These methods generally require suturing of the vascular tissue, which can be difficult and time-consuming to carry out.

Figure 12:
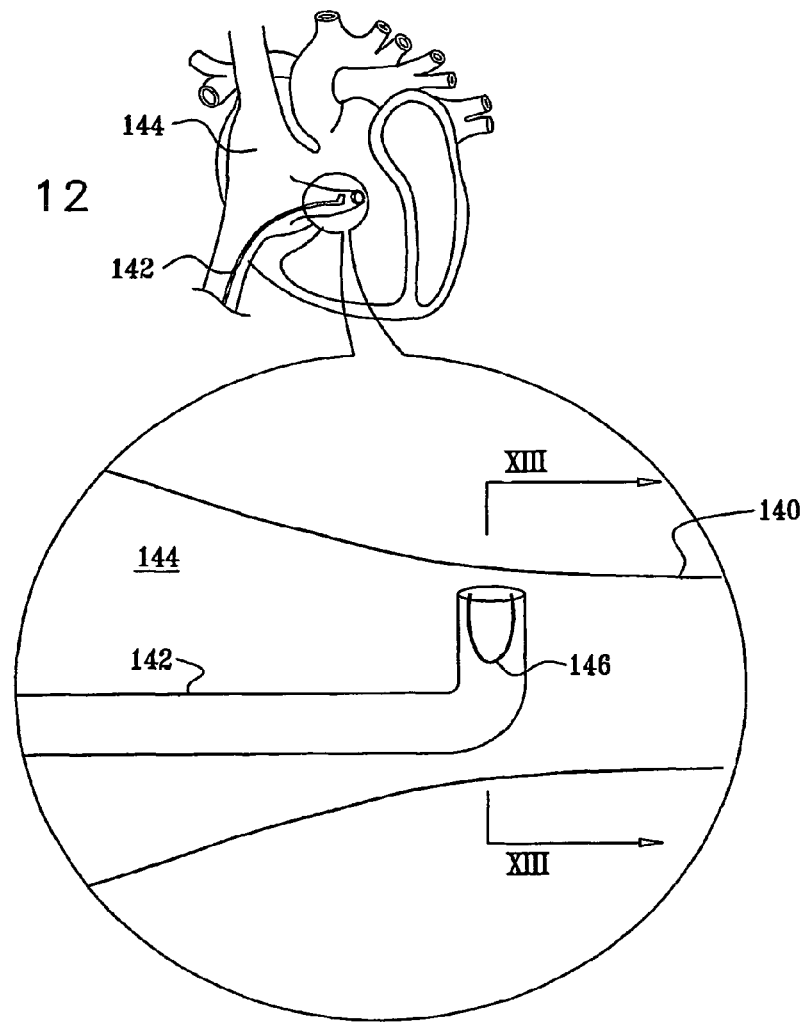
FIG. 12 is a schematic side view of a vascular structure, in which a catheter is inserted for deployment of a constricting clip, in accordance with an embodiment of the present invention.

In contrast to these methods and to the preceding embodiments, FIG. 12 schematically illustrates a method for constricting the diameter of a vascular structure without the use of sutures or a stent, in accordance with an alternative embodiment of the present invention. The embodiment is illustrated here with reference to reducing the diameter of a coronary sinus 140 of a patient, although this method is also applicable to other vascular structures. A catheter 142 is inserted through a right atrium 144 of the patient into coronary sinus 140. The catheter is bent at its distal end, as shown in the figure, to permit convenient deployment of a constricting clip 146, as described below.

Figure 13A:
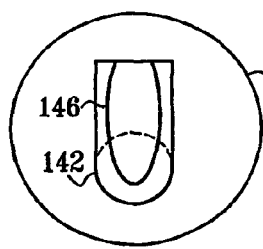
FIGS. 13A-C are schematic, sectional views of the vascular structure of FIG. 12, taken along a line XIII-XIII in FIG. 12, showing stages in the deployment of a constricting clip, in accordance with an embodiment of the present invention.
Figure 13B:
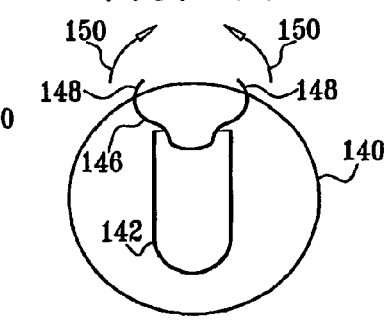
Figure 13C:
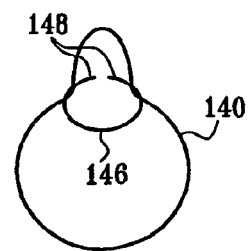

FIGS. 13A-C are schematic, sectional views of coronary sinus 140, taken along a line XIII-XIII in FIG. 12, showing stages in the deployment of clip 146, in accordance with an embodiment of the present invention. Clip 146 typically comprises a super-elastic material, which is formed so that in its relaxed state, it has an approximately closed form, as shown in FIG. 13C, for example. During insertion of catheter 142 into the coronary sinus, however, clip 146 is compressed within the distal end of catheter 142, as shown in FIG. 13A.

Once catheter 142 has been advanced into coronary sinus 140, a deployment mechanism, such as a pusher (not shown) inside the catheter, is actuated in order to advance clip 146 out of the distal end of the catheter. As a result, the clip opens up into the configuration shown in FIG. 13B. Ends 148 of the clip catch the tissue of coronary sinus 140 at two points that are spaced apart on the wall of the coronary sinus. The elasticity of clip 146 causes the ends of the clip to draw together as the clip is advanced further out of the catheter, as illustrated by arrows 150. Finally, when the clip has advanced completely out of the end of the catheter, ends 148 close in toward one another and pinch together the portion of the vascular tissue that is located between the clip ends. The result, as seen in FIG. 13C, is that the effective diameter of coronary sinus 140 is reduced.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. A system for delivery of an implant having an implant lumen to a target position in a body passage, the system comprising:
   an elongate tubular sheath comprising an elastic material, wherein the tubular sheath is configured to be passed through the body passage while containing the implant in a compressed state inside the sheath, and wherein the sheath has a distal end with an aperture formed therein;
   a catheter having a proximal end and a distal end and a lumen that extends between the proximal end and the distal end, wherein the lumen distends at the distal end thereby forming a compressible distended portion, wherein at least a portion of the catheter is disposed within the implant lumen, and the compressible distended portion is configured to slidably open and slidably obstruct the aperture;
   an ejector configured to move relative to the catheter and to force the implant in a distal direction thus stretching the elastic material of the tubular sheath so as to expand the aperture of the tubular sheath; and
   wherein when the compressible distended portion of the catheter slidably opens the aperture and the aperture expands, the implant is delivered to a target position in a body passage.

2. The system of claim 1, wherein the catheter lumen passes through the compressible distended portion, and wherein the catheter is sized to slidably receive a guidewire.

3. The system of claim 1, wherein the compressible distended portion has a non-compressed diameter that is sized to obstruct the aperture.

4. The system of claim 1, wherein the implant comprises first and second ring members coupled together, each having an expanded configuration and a collapsed configuration, wherein the first and second ring members are discrete and separated from one another by a gap region having a smaller diameter than the first and second ring members, wherein the smaller diameter reduces a flow through the body passage at the target position in the expanded configuration.

5. The system of claim 4, wherein the compressible distended portion is compressible to a diameter that is smaller than a diameter of the gap region in the implant.

* * * * *